(12) United States Patent
Tjioe et al.

(10) Patent No.: US 8,848,991 B2
(45) Date of Patent: Sep. 30, 2014

(54) DENTAL SHADE MATCHING DEVICE

(75) Inventors: Soek Gam Tjioe, Kowloon (HK); Weng Kong Tam, Kowloon (HK)

(73) Assignee: Soek Gam Tjioe, Kowloon (HK)

( * ) Notice: Subject to any disclaimer, the term of this patent is extended or adjusted under 35 U.S.C. 154(b) by 400 days.

(21) Appl. No.: 13/422,800

(22) Filed: Mar. 16, 2012

(65) Prior Publication Data
US 2013/0244197 A1 Sep. 19, 2013

(51) Int. Cl.
G06K 9/00 (2006.01)

(52) U.S. Cl.
USPC .......................................... 382/128; 382/131

(58) Field of Classification Search
None
See application file for complete search history.

(56) References Cited

U.S. PATENT DOCUMENTS 7,142,196 B1 * 11/2006 Connor et al. ................. 345/173
7,773,095 B1 * 8/2010 Badrak et al. ................. 345/619
2003/0148243 A1 * 8/2003 Kerschbaumer et al. ........ 433/29
2007/0141528 A1 * 6/2007 Kobayashi ....................... 433/29
2011/0221880 A1 * 9/2011 Liang et al. ...................... 348/77

OTHER PUBLICATIONS

Dental color matching instruments and systems. Review of clinical and research aspects Stephen J. Chu ; Jul. 2010.*

* cited by examiner

Primary Examiner — Nancy Bitar
(74) Attorney, Agent, or Firm — McNeely, Hare & War LLP; Kevin J. McNeely, Esq.

(57) ABSTRACT

A non-contact type dental shade matching device is provided, comprising a camera body for capturing image of one or more target teeth; an opaque intra-oral compartment snugly adapted for a human mouth; an opaque cover shield body connected between the camera body and the intra-oral compartment; one or more holders for holding one or more shade tabs; and a color matching module being operably connected to the camera body to receive the captured images containing color and translucency information of the target tooth and/or shade tab information, and then to process the images based on a content-based algorithm for automatic shade matching between the target tooth and the shade tabs for each of the captured images, so as to achieve an optimal dental prosthesis.

21 Claims, 4 Drawing Sheets

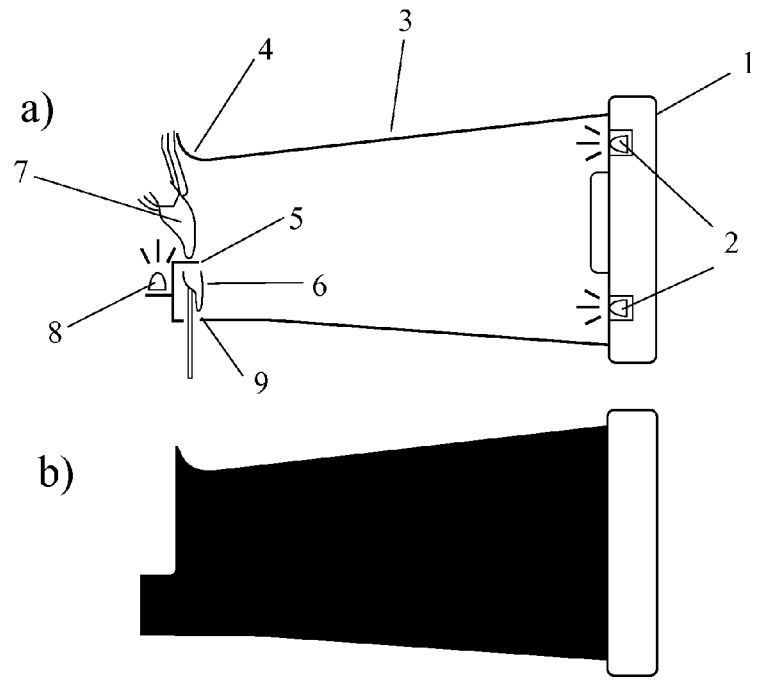
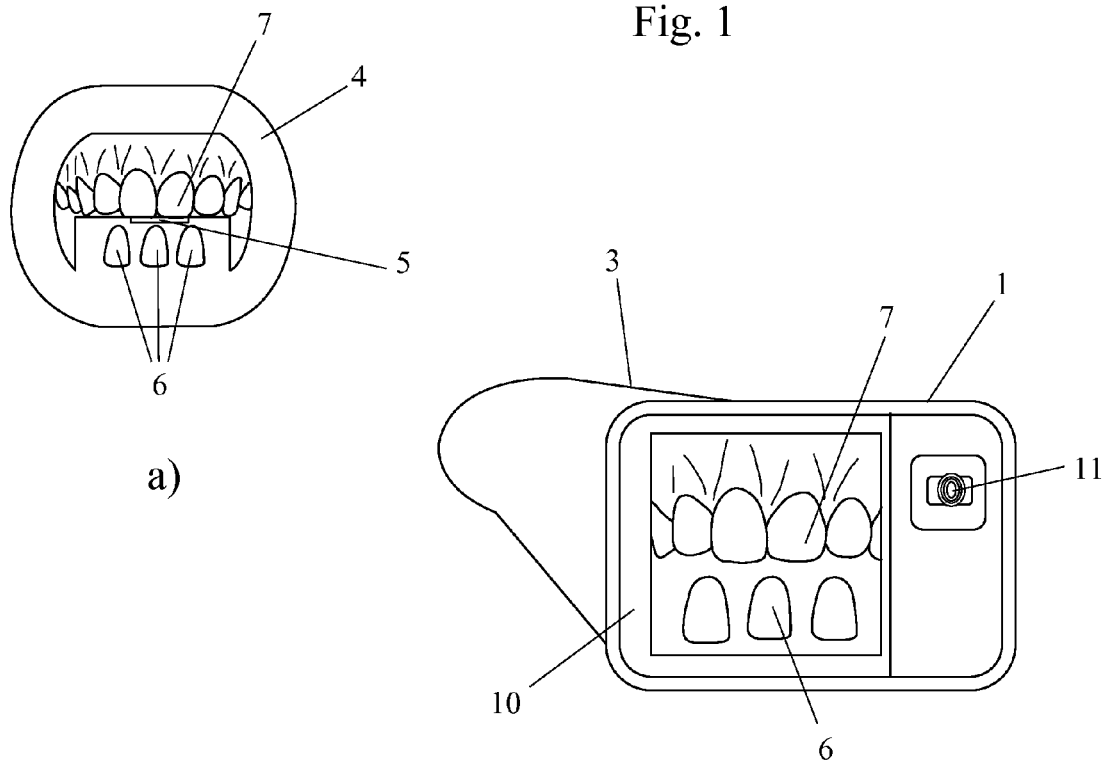
Fig. 1
Fig. 2

DENTAL SHADE MATCHING DEVICE

FIELD OF THE INVENTION

The invention relates to color and translucency selection for fabrication of dental prosthesis, in particular to a dental shade matching device which allows for cost-effective fabrication of the optimal dental prosthesis.

BACKGROUND OF THE INVENTION

Dental shade (color) matching is an important procedure in prosthetic treatment. In order to achieve the best restoration quality, dental color should be selected so that the color shows harmonic effects. Traditionally, the dentists perform the dental shade matching by visual selection using the shade tabs of the commercial dental shade guide. With such visual color selection, errors are often introduced since the visual selection heavily depends on the sense of color by individual professionals.

Recently, expensive contact-type instruments were employed in the dental practice. Most of the prior art products which employ either spectrophotometer or colorimeter for measuring color features in La*b* or HSV space.

The disadvantages of the spectrophotometer or colorimeter devices include one or more of the following.

1. They are not suitable for measuring the tooth surface that is non-flat in nature.
2. Their small view window cannot cover the whole tooth surface that provides essential information of color gradation.
3. Their algorithms are insufficient in the provision of color description of surface texture.
4. They do not provide neighboring tooth image for comparison.
5. They are difficult to be correctly positioned over the target tooth surface.
6. Only one type of color spaces is used to acquire the color information, which may be not accurate in some cases, as a result of the influence of light, environmental conditions and the like.
7. They also cannot solve the problem of metamerism effect caused by different light reflection properties between the tooth and the prosthesis materials.

Other instruments have been reported, for example, in US Patent Application No. 20030148243A1 and US Patent Application No. 20070141528A1.

In US Patent Application No. 20030148243A1, there is disclosed a dental camera and a mouthpiece attachment therefor. The camera has a light source and a light receiving element configured for receiving reflected light and producing an image based on the received light. The mouthpiece is mountable to the housing of the camera and is configured for contacting a patient's mouth for positioning the camera with respect to at least a portion of the mouth. The mouthpiece has a light channel associated with the light source for permitting the emitted light to reflect off a tooth in a patient's mouth and permitting the reflected light travel into the receiving element. A wing extends radially from the light channel and configured and dimensioned for placement between a lip and teeth of a patient for substantially blocking light from entering the light channel from outside the wing. A display on the housing is associated with the receiving element for displaying the image. A sound receiving element on the housing allows a dentist to record voice comments and stores them in connection with the images.

Another US Patent Application No. 20070141528A1 discloses a contact cap which is attached to a top cover of a camera of a dental tooth measuring apparatus, and when shooting, positioning of the tooth to be measured is performed with a bite section being slightly bitten by both of adjacent teeth sandwiching the tooth to be measured, and with keeping a state where the inside of the adjacent teeth is in contact with a camera side surface of a positioning convex section. Positioning of the tooth to be measured and the adjacent teeth with variation among individuals with respect to the camera can be performed more precisely.

Therefore, there is a need in the art for accurate dental shade matching and cost-effective fabrication of dental prosthesis.

SUMMARY OF THE INVENTION

The present invention has been developed to fulfill the needs noted above and therefore has a principle object of the provision of a novel dental shade matching device, comprising:

a camera body for capturing image of one or more target teeth, and having at least one chromatic illuminant module to emit chromatic light;

an opaque intra-oral compartment snugly adapted to be received in a human mouth, said intra-oral compartment having a soft tissue retracting part for retracting the soft tissue around the target tooth, and a stop for supporting the target teeth in a desirable orientation;

an opaque cover shield body having one end attached tightly to the camera body and another end connected to the intra-oral compartment;

one or more holders for holding one or more shade tabs in place and releasably attached to the intra-oral compartment; and a color matching module comprising a microprocessor, said color matching module being operably connected to the camera body to receive the captured images containing color and translucency information of the target tooth and/or shade tabs, and then to process the images based on a content-based algorithm, preferably a content-based image retrieval (CBIR) algorithm, for automatic shade matching between the target tooth and the shade tabs for each of the captured images, so as to achieve an optimal dental prosthesis.

The term "content-based algorithm" herein refers to an algorithm that compares tooth shade information based on the content that is related to colors, shape, textures or any other information that can be derived from the tooth image. The shape of the content is defined as a rectangular area to avoid the influent by light shadow in the lateral and cervical borders of the tooth or shade tab images. This algorithm helps to retrieve the shade tab images based on similarities in their contents (textures, colors, shapes etc.). The color content of the tooth image may be cropped manually by user or automatically by computer.

The camera body may be a CCD/CMOS-based digital camera for capturing the images in non-contact manner.

The soft tissue retracting part is used as a lip retractor for placement on the target tooth in the mouth.

In one embodiment of the invention, the dental shade matching device further comprises a translucent illuminant module placed on the stop of the intra-oral compartment. Preferably, the stop is an incisal/occlusal stop having a protrusion extending toward the mouth, and the translucent illuminant module is placed on the protrusion.

The chromatic illuminant module may provide specific frequencies of visible light emitted at sequential time intervals, and the camera body captures a series of images under all these illumination separately or sequentially.

The color and translucency information of the target tooth and/or the shade tabs may be processed in situ or electronically transferred to an external system where the images are processed or stored. For example, the camera body may further comprise a digital connection interface, enabling the wireless or cable transfer of the data captured and/or analyzed by the camera body to the external system, such as the PC, an internet server or a laboratory location, where the image and the results may be processed or stored. A control panel may be provided in the camera body and the control panel may be designed as simple as possible to facilitate clinical uses.

Preferably, a plurality of the chromatic illuminant modules are provided and installed in a ring-shape mount to surround a lens of the camera body.

The holder for holding the shade tabs may be formed as a supporting space for holding a rod or strip of the shade tab.

In one preferred embodiment of the invention, the algorithm comprises:

image preprocessing where each of the images is segmented into a plurality of sections and noise is removed, color features extraction where the color features of the image is extracted and reassembled into a plurality of color feature sets, and similarity measurement where the target tooth and the shade tabs are compared and analyzed for their contents to determine an optimal shade candidate.

For each of the images, only a part of the target tooth or the shade tab, which is not influenced by light shadow on the lateral and cervical borders of the tab or the target tooth, is cropped to represent its content.

The color contents may be subject to noise mainly from over reflection of flashlight on most contour areas, these areas are removed in order to prevent from affecting shade feature, the noise is removed by a fixed intensity threshold which is adopted to filter the over-reflective areas, so that refined color contents are used for further shade matching.

In order for the more effective comparison, the contents of the target tooth in the image may be divided into an array of blocks, each of which is analyzed for comparison of the color features with the shade tabs.

Advantageously, one or more virtual color spaces are used in the algorithm for tooth color measurement. The color features in the color spaces are extracted from each of the blocks, and the statistic measurements for the similarity measurement are calculated for the block to describe the color feature thereof. The virtual color space is constructed by one or more vector of different color space systems selected from the group consisting of color spaces: HSV, RGB, XYZ, Lab and Luv . . . etc., or a combination thereof. More preferably, the virtual color space is selected from:

Sa*b* color space, wherein S comes from HSV space, a* and b* come from L*a*b* space, and wherein S means saturation representing the degree of color saturation, a* represents a measurement of the redness (+a*) to the greenness (−a*), and b* represents a measurement of the yellowness (+b*) to the blueness (−b*).

According to the invention, the color matching module performs the calculations for each of the above virtual color spaces using a statistic training/prediction method, preferably Support Vector Machine (SVM), to compare results of the color matching obtained from the virtual color spaces, thereby selecting the optimal color space for fabrication of the dental prosthesis.

A distance between the contents can be defined as a summation of all individual block distances within the content, and the similarity between two contents is measured by the measurements of the block distances. The distance between the two corresponding blocks in contents s and t is defined as:

$$\mathrm{dist}(s,t) = (\Sigma_i (b^s(i) - b^t(i))^2)^{1/2},$$

where i is the block label within the content, $1 \leq i \leq m \times n$; $b^s$ and $b^t$ are the blocks in contents s and t, respectively.

A statistical classification algorithm selected from the group consisting of: Support Vector Machines (SVM), neural network (multi-layer perception), k-nearest neighbors, Gaussian mixture model, Gaussian, naive Bayes, decision tree, radial basis function classifiers, and any combination thereof, may be used in the algorithm of the invention.

In one preferred embodiment of the invention, the color matching module is programmed to produce various prosthesis models according to existing data stored therein, and the captured color and translucency information is compared and analyzed directly with the produced models for the automatic shade matching between the target tooth and the shade tabs.

To perform a perfect color matching, the target tooth/teeth may be placed clearly in the center of the image including information of surrounding structures. In some cases, the shade tabs are required for reference or confirmation. The translucency property of the prosthesis materials is also of importance to reveal a perfect matched porcelain layers being used. These features are achieved by the design of the intra-oral compartment, which may comprise an incisal/occlusal stop for easily placing the target tooth in required orientation and proportion.

After the correct placement of the intra-oral compartment of the dental shade matching device in the oral cavity, the user simply turn on the camera and presses a shutter button on the camera body to capture a series of images at one touch for color matching purpose.

The dental matching can be done automatically through the color matching module which is formed by a microprocessor mounted internally or externally relative to the dental shade matching device, for example in the camera body or in the server positioned in the dental laboratory. The color information and analysis on the tooth surface is collected and processed through, for example, the automatic color content retrieval and model-based matching algorithm. The device of the present invention reveals that the content-based algorithm gives a good matching result under open/uncontrolled condition, which is comparable to the result of using spectrophotometer under contact measurement. The improvement and advancement of the content-based algorithm is employed in the present invention to make it more feasible to be used in clinical environment. The expected matching accuracy will have much improvement in the invention since the external condition of the device is shielded and other parameters are controllable.

Additional advantages of the dental shade matching device may include one or more of the following.

1. The non-contact type CCD/CMOS sensor is used to capture the whole tooth surface for dental color analysis and comparison.

2. Different chromatic illuminants would be projected on the tooth surface for comparing different metamerism effects produced by enamel, dentin or dental material of different properties.

3. The advanced shade matching algorithm is used for better acquirement of the tooth color and translucency information.

4. The invention has successfully solved the bottleneck of current remote denture manufacturing by transmitting both the crystal clear teeth image and the appropriate well-positioned shade tabs thus captured at the same time between the technicians and the dentists for dental shade communication. This arrangement will minimize the error of color fabrication caused by the dental laboratories especially when remote manufacturing of prostheses are prescribed by the clinicians.

To have a better understanding of the invention reference is made to the following detailed description of the invention and embodiments thereof in conjunction with the accompanying drawings.

BRIEF DESCRIPTION OF THE DRAWINGS

FIG. 1a) shows an internal view of the dental shade matching device constructed according to one preferred embodiment of the invention;

FIG. 1b) shows a lateral view of the dental shade matching device of FIG. 1a);

FIG. 2a) shows an internal view of the intra-oral compartment of the device of FIG. 1a);

FIG. 2b) shows a back view of the device of FIG. 1a);

In the various figures of the drawings, like reference numbers are used to designate like parts.

DETAILED DESCRIPTION OF THE INVENTION

Figure 3:
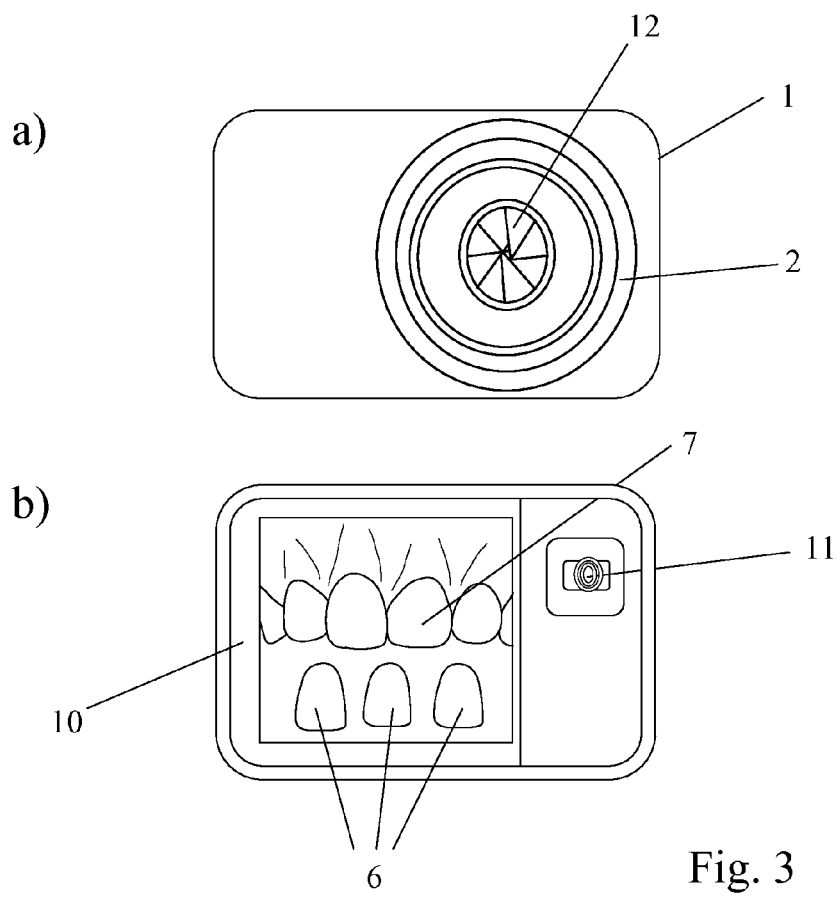
FIG. 3a) shows a front view of the camera body of the dental shade matching device of FIG. 1a)
FIG. 3b) shows a back view of the camera body of FIG. 3a)

Structure and Operation of the Present Invention

While this invention is illustrated and described in preferred embodiments, the dental shade matching device may be produced in many different configurations, sizes, forms and materials.

Referring now to the drawings, FIGS. 1a) to 2b) provide a dental shade matching device constructed consistent with a preferred embodiment of the present invention. In this embodiment, the dental shade matching device comprises a digital camera body 1, a cover shield body 3 and an intra-oral compartment, all of which are opaque.

The digital camera body 1 is preferably a digital camera of non-contact type and/or is CCD/CMOS-based. In this embodiment, the camera body is additionally provided with multiple chromatic illuminant modules 2 that are specially designed to emit specific frequencies of visible light (for example white, red, blue and/or yellow light) at sequential time intervals. The multiple chromatic illuminant modules 2 are installed in a ring-shaped mount to surround a lens of the camera body. Also, a general electronic ring flash is possible. A series of images of the target tooth under all these illumination will be captured separately or sequentially.

The camera body 1 may further comprise a digital connection interface, enabling the color and translucency information of the target tooth and/or the shade tabs to be electronically transferred to an external system for example a personal computer (PC), an internet server or a laboratory location, where the images are processed. It would be appreciated that the above information may be processed in situ by a control panel arranged on the outer surface of the camera body. The control panel may be designed as simple as possible to facilitate clinical uses.

The cover shield body 3 is designed to eliminate the illuminant alteration from outside of the mouth, and can be of any shape to allow proper placement of the intra-oral compartment in the mouth of a patient without light permeation or transmission. The cover shield body 3 has one end tightly connected to the camera body 1. This arrangement ensures that no external light permeates into the internal cavity of the device to cause an adverse effect on the captured images.

The intra-oral compartment comprises a soft tissue retracting part 4 for retracting the soft tissue around the target tooth 7 to be imaged. The retracting part 4 is connected to the other end of the cover shield body 3. In this embodiment, the retracting part 4 is used as a lip retractor to facilitate the placement of the cover shield body inside the mouth. The intra-oral compartment further comprises an incisal/occlusal stop 5 for easily placing the target tooth in the required orientation and proportion, for example in the center part of the images. Below the incisal/occlusal stop 5, there is a holder 9 on which a selected shade tab 6 is placed to serve as a reference for color matching. In this embodiment, the holder 9 is formed as a supporting space for holding a rod or strip of the shade tab, which is made of metal, resin or plastic material. The shade tab 6 can be mounted in the holder 9 mechanically, for example by snap-fit or screwing, allowing image taking of the tabs 6 by the camera body 1.

As illustrated in FIG. 1a), the incisal/occlusal stop 5 has a protrusion extending toward the mouth. On the protrusion is mounted a translucent illuminant module 8 which is an important back light source for acquiring translucency information of the target tooth for the fabrication of the prostheses. Because the translucent illuminant module 8 is arranged behind the target tooth 7 and the shade tab 6, the translucency information of the tooth and the tab may be acquired to fabricate more accurate prosthesis. Such an arrangement for acquiring the translucency information is provided for the first time in the industry of restorative prosthesis.

Advantageously, the dental shade matching device further comprises a color matching module for processing the digital images of the target tooth 7 and a shade tab 6 taken by the camera body using a novel matching algorithm, which will be herein below described in detail. The color matching module may be provided internally or externally, for example in the camera body 1 or in a remote server.

FIGS. 2a) and 2b) respectively illustrate the internal and back views of the intra-oral compartment with the images of the target tooth 7 and the shade tabs 6 viewed from the screen and control panel 10. In this embodiment, the screen and control panel 10 is the type of LCD or LED touch screen. Alternatively, the control panel and the LCD or LED screen may be provided separately on the camera body. A shutter button 11 is positioned on the camera body 1 for capturing images.

As can be seen in FIG. 2a), the lip tissue is distracted away from the teeth by the soft tissue retracting part 4 for placement of the cover shield body in the mouth. The upper row of FIGS. 2a) and 2b) is the target tooth 7, the lower row is the shade tabs 6 held by the holder 9. The incisal/occlusal stop 5 is positioned between the target tooth 7 and the shade tabs 6 for easy placement of the target tooth 7 in the required orientation and proportion. The cover shield body 3 is fixed at its one end onto the camera body 1, as illustrated in FIG. 2b).

The dental shade matching device of the invention can capture the images of the target tooth, the neighboring teeth and the shade tabs. Therefore, the real time color and translucency matching and comparison between the target tooth and the shade tabs can be performed quickly.

FIG. 3a) is a front view of the camera body 1, with the cover shield body 3 being removed. FIG. 3b) is a back view of the camera body. The cover shield body 3 may be mounted on the camera body 1 mechanically, such as by screws, snap-fit, adhering, or any suitable method known in the art, which would be within the ability of a person of ordinary skills in the art. The camera body 1 comprises a lens 12 and the multiple chromatic illuminant modules 2 of ring flash.

The Content-Based Algorithm of the Present Invention

Shade selection in dental practice is an important but difficult task. Dentists are always challenged to satisfy the aesthetic requirement of patients by selecting the correct shades to match the natural teeth during fabrication of prosthesis. Most dental professionals are lack of knowledge in color science as well as in matching among similar colors. During the shade selection, certain conditions have to be confirmed in order to have a perfect match of the tab with the natural teeth. In the procedure of prostheses fabrication, dentists and technicians need to communicate on teeth colors. However, verbal communication of color differences is limited. Usually the clinical dentist professionals have to make the decision of shade selection from the patients' teeth themselves. The more precise dental colors can be described, the more accurate porcelain colors can be delivered. The result of shade matching seems to be a very important role that directly relates to the quality of prostheses. A correctly selected shade usually results in high quality prostheses in which the colors of the fabricated prostheses are harmonic to that of the neighboring teeth and can hardly be distinguished.

Recently, up-to-date technologies and products of digital imaging have been widely found in the field of dentistry for the prosthesis fabrication. The most common example is the usage of mega-pixel digital cameras for capturing intra-oral images, and computer is employed to estimate the possible shade tabs or shade zone over the whole tooth.

In the color science, a color in the visible spectrum supposes to be a composition of three-dimensional vector features. Most of the colors visible to human eyes can be described in terms of vector features inside a specified color space. In the color spaces proposed by scientists, the most popular VGA monitoring system uses RGB color space, in which three vector features, namely red, green and blue, are used to represent a specific color. Munsell proposed a HSV color space described by hue, value and chroma (saturation). Hue represents families of color such as red, green and blue. Value is the lightness from black to white. Chroma or saturation is the degree of color saturation. In 1931, the Commission Internationale de l'E'clairage (CIE) established XYZ color space composed of tristimulus values representing the human vision responds to a given color. In 1976, CIE further defined an L*a*b* color space based on the color receptors of human eyes. The attribute value L* indicates the lightness of an object. The value a* represents a measurement of the redness (+a*) to the greenness (−a*), and the value b* represents a measurement of the yellowness (+b*) to blueness (−b*). American Dental Association (ADA) announced the regulation of using ΔE of L*a*b* color space for measuring color differences of dental materials, which is defined as:
$$\Delta E = \{(L^*_i - L^*_j)^2 + (a^*_i - a^*_j)^2 + (b^{*i} - b^*_j)^2\}^{1/2}.$$

The invention provides a system using a content-based algorithm, for example a content-based image retrieval (CBIR) algorithm, for automatic shade matching in the dentistry. The system consists of three major parts: image preprocessing, color features extraction and similarity measurement. In the part of image preprocessing, each of the shade images is segmented into a plurality of small regions for further analysis and noise is removed. In the part of color features extraction, the color features are extracted and reassembled into a plurality of useful color feature sets. In the part of similarity measurement, test regions are matched with the shade tab samples in the database using the CBIR algorithm which will be explained herein below. A predicted shade tab candidate is obtained finally when the similarity measurement between the test and sample shades (i.e. the target tooth and the shade tabs) is minimized.

According to the present invention, after the correct placement of the intra-oral compartment of the dental shade matching device in the oral cavity, the user simply presses the shutter button 11 on the camera body to capture a series of images at one touch for color matching purpose.

In each of the images captured, only a part of the target tooth or the shade tab is cropped for example manually to represent its content. The main purpose of the cropping is to prevent the content from being influenced by light shadow on the lateral and cervical borders of the tab. The content's width and height shall be kept as wide and tall as possible in the way that neither of its corners lay outside the tab.

The color contents are subject to noise mainly from over-reflection of flashlight on most contour areas. It is necessary to remove these areas in order to prevent from affecting shade feature. Noise removal by a fixed intensity threshold, learnt through image samples, is adopted to filter the over-reflective areas. The refined color contents are then used for further processing.

Figure 4:
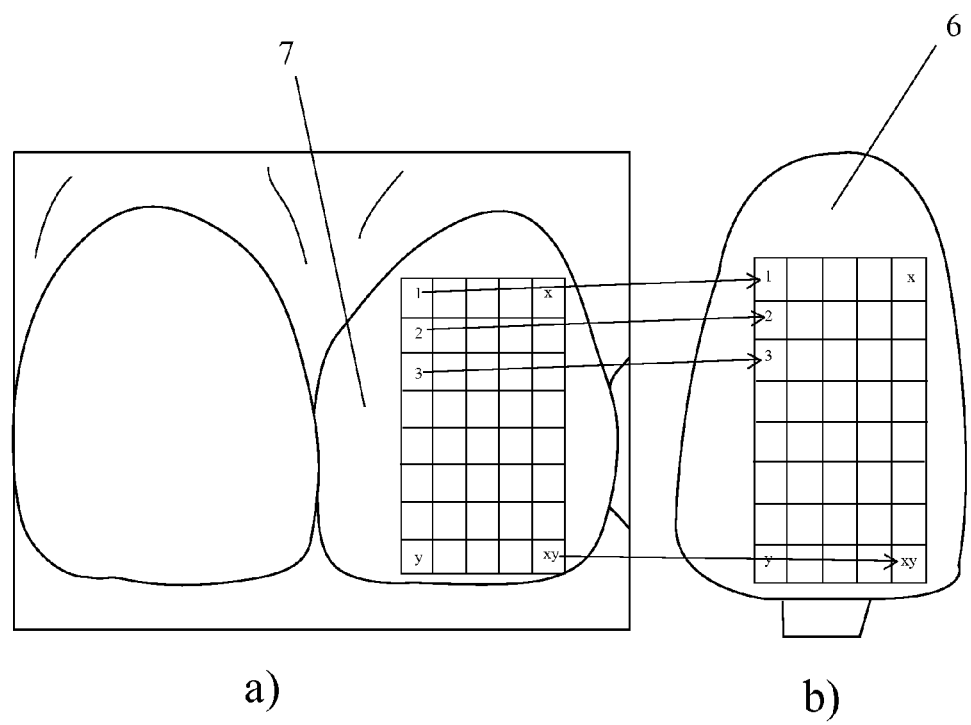
FIG. 4a) shows a target tooth analyzed by an automatic color content retrieval and matching algorithm.
FIG. 4b) shows a shade tab sample matchable with the target tooth of FIG. 4a) according to the algorithm.

In order for the more effective comparison, the contents of the target tooth in the image are divided into X×Y small blocks, each of which is analyzed for comparison of the color features with the corresponding shade tabs. The division helps detailed comparison, but increases the computational complexity. In FIGS. 4a) and 4b), the image is divided into 8×5 small blocks, where X=8 and Y=5.

FIGS. 4a) and 4b) illustrates the automatic color content retrieval and matching algorithm showing a match between the target tooth and a shade tab sample. Both the target tooth 7 in FIG. 4a) and the shade tab 6 in FIG. 4b) are divided into 8×5 blocks. The color or shade of each of the blocks is measured, retrieved and compared between the target tooth and the shade tabs to select the optimal shade tab for the prosthesis fabrication.

The effects of using different color spaces in teeth color measurement have been studied and evaluated in the invention. The color features in these spaces are extracted from all individual blocks within the color content in four common color spaces (RGB, HSV, XYZ, L*a*b* and Luv, etc.). Statistic measurements (mean values) for similarity measurement are calculated for each block to describe its color feature.

The content distance is defined as the summation of all individual block distances within the content. The distance between two corresponding blocks in contents s and t is defined as:

$$\text{dist}(s,t) = (\Sigma_i (b^s(i) - b^t(i))^2)^{1/2},$$

where i is the block label within the content, $1 \leq i \leq m \times n$; $b^s$ and $b^t$ are the blocks in contents s and t, respectively.

To find out the suitable feature color spaces among the four common color spaces, the precision of matching under the four common color spaces is compared using the first group samples. Here, the precision of matching is defined as the number of correct matches out of the attempt trials. This process helps to find out the suitable color spaces used. The comparison reveals that HSV and L*a*b* have the precision rate higher than the others.

Further investigations focus only on the color features extracted from the two impressive color spaces, HSV and L*a*b*. Individual feature comparison shows that there is a high matching rate of S feature in HSV than the others. Though the L*a*b* color space also has a good rate of matching, L* component does not have good accumulative effect in the overall result and is not considered to be a good feature.

Finally, S in the HSV space, a* and b* in the L*a*b* space are selected to be the representative features to form a new virtual color space Sa*b*, wherein S means saturation representing the degree of color saturation, a* represents a measurement of the redness (+a*) to the greenness (−a*), and b* represents a measurement of the yellowness (+b*) to the blueness (−b*). That is, these three features, S, a* and b*, are used to reassemble a new feature set which does not represent a real color space known in the art.

Alternatively, Sa*b* or any feature combination can be used to reassemble another new feature set, which do not represent a real color space in the art as well.

It would be noted that any combination of vectors of different color space systems (for example, the four common color space, HSV, RGB, XYZ and Lab) or a combination thereof can be taken to form a new virtual color space, which is specially used for the purpose of dental shade matching. The color matching module of the present invention is programmed to perform calculations for each of the above new virtual color spaces using a statistic training/prediction method (for example Support Vector Machine, SVM) to compare the precision of color matching among these new virtual color spaces and to select the optimal shade tab for the fabrication of prosthesis.

Many measurements and analysis are carried out to compare the performance using these new feature sets of color spaces. The measurements reveal that the new color space, Sa*b*, has much more matching precision than the conventional color spaces including RGB, XYZ, HSV, L*a*b*, or ΔE of L*a*b*. It has been found in the invention that, in the color science of dentistry, chroma and intensity values have potentially influence on the matching precision. The results obtained according to the invention reveal that high chroma and low intensity shades could be matched with higher accuracy.

The matching process of the invention can be done automatically through the color matching module comprising a microprocessor which may be arranged inside the device or remotely in dental laboratory. The color analysis and matching on the tooth surface is calculated using the automatic color content retrieval and model-based matching algorithm. The content-based algorithm is found to give a good matching result under open/uncontrolled condition, which is comparable to the result of using spectrophotometer under contact measurement. The improvement and advancement of the content-based algorithm of the invention makes it possible and more feasible to be used in clinical environment. The expected matching accuracy will have much improvement according to the invention, since the external condition of the device is shielded and eliminated, and other parameters are controllable.

To perform a perfect color matching, the target tooth/teeth may be placed clearly in the center of the image including the information on surrounding structures. In some cases, the shade tabs are required and the images thereof are captured by the camera body for reference or confirmation. The translucency property of the prosthesis materials is also of importance to reveal a perfect matched porcelain layers being used. These features are achieved by the design of the intra-oral compartment.

Figure 5:
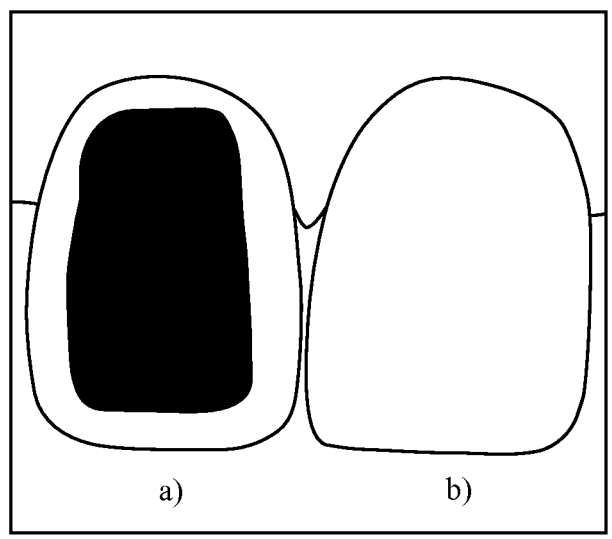
FIGS. 5a) and 5b) show the translucency difference between a porcelain-fused-to-metal crown and a full ceramic crown acquired by the featured translucency comparison preformed in the dental shade matching device, wherein FIG. 5a) denotes an opaque prosthesis material, and FIG. 5b) denotes a translucent prosthesis material.

FIGS. 5a) and 5b) illustrate the featured translucency comparison in the dental shade matching device showing the difference between a porcelain-fused-to-metal crown and a full ceramic crown, under the illumination of the translucent illuminant module 8. The images of FIGS. 5a) and FIG. 5b) are captured and analyzed in the same way according to the CBIR algorithm of the invention, reference of which may be made to FIG. 4a) and FIG. 4b). The translucency information needs to be considered when the physical prosthesis is fabricated, in order to provide better effect. The translucency property depends primarily on the prosthesis materials. The black zone of FIG. 5a) denotes that the material is not translucent, and the material of FIG. 5b) is light-translucent.

It is the first time in the art of dental industry that the translucency comparison among the different shade tabs or the translucency comparison between the target tooth and the shade tab is used to fabricate and achieve the better restorative prosthesis. The prior art technology uses the grayscale information to represent the translucency of the prosthesis material, which may causes incorrect translucency information, because some shade tab materials having similar reflection properties may have different transparency properties. For example, the color of a shade tab made of metal materials may be similar to that of a shade tab made of plastic materials, but the former is generally opaque, and the latter is likely light-transparent. The invention has successfully solved this problem by providing the backlight using the translucent illuminant module 8. In addition to their reflection properties, the transparency information of the candidate shade tabs acquired by the device of the invention enables the selection of the optimal shade tab relative to the target tooth and the comparison between the fabricated prostheses and the target tooth.

According to the invention, the shade matching between the target tooth and the shade tabs can be model-based or distance measurement. The model-based device is configured to automatically train any color features from the preset color spaces. In particular, the color matching module is programmed to produce various prosthesis models according to the existing data stored therein, and the extracted color and translucency information from the captured images is compared and analyzed directly with the produced models to find out the most matchable model, which leads to reduced time for the automatic shade matching and more accuracy of fabricating the optimal restorative prosthesis.

As discussed above, by using the distance measurement, the similarity of the two color contents is measured by content distance between them. The distance measurement is established by calculating the summation of all individual block distances within the contents.

Figure 6:
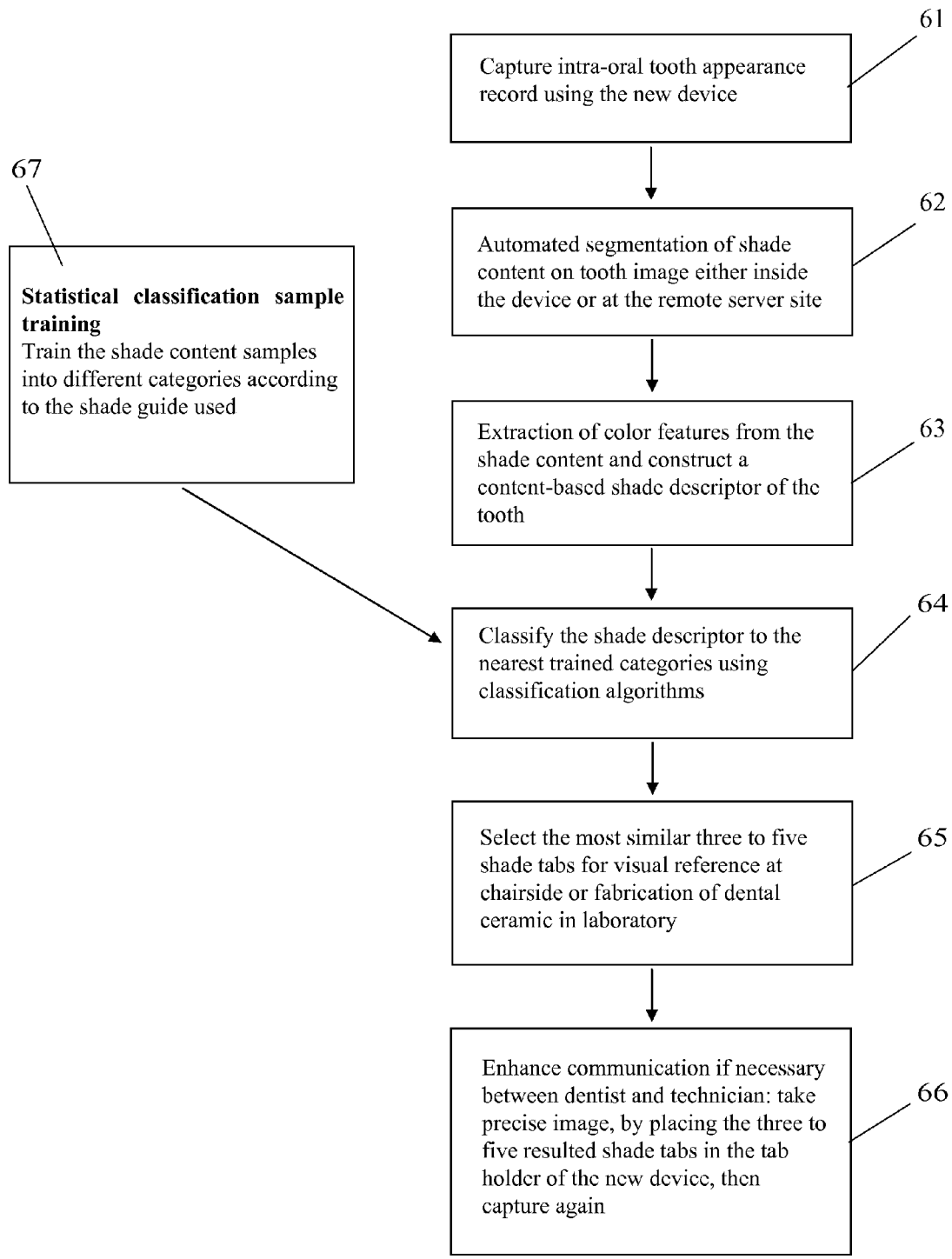
FIG. 6 shows a work flow chart of the dental shade matching device according to the invention.

FIG. 6 is an exemplary work flow chart of the dental shade matching device according to the invention.

The image of the intra oral tooth appearance and record is captured by the camera body 1 at step 61. The target tooth, i.e. the tooth to be treated, will not come into contact with the camera body 1 during the image capturing. The target tooth, the neighboring tooth, and optionally one or more shade tabs may be captured in a single image for ease of comparison. In this step, a plurality of images may be taken by the camera body 1 using the chromatic illuminant modules 2 emitting visible light of different colors and the translucent illuminant module 8 positioned behind the shade tabs 6.

The color and translucency information of the target tooth and/or the shade tab samples may be processed by the color matching module inside the device, or electronically transferred to a remote computer, server or laboratory for processing. At first, the shade content on the images will be automatically segmented into X×Y small blocks at step 62, as described above and shown in FIG. 4*a*) and FIG. 4*b*).

The color features are then retrieved (extracted) from the color or shade contents to construct a content-based descriptor of the target tooth at step 63 according to the above automatic color content retrieval and model-based matching algorithm. In particular, the reassembled feature combination, for example, the parameters S in the HSV space, a* and b* in the L*a*b* space, are retrieved and used to construct the descriptor.

At step 64, the color or shade descriptors are classified into the nearest trained categories using the statistical classification algorithms. In the classification algorithms (see step 67), the statistical classification sample training is used to allow the training of the color or shade content samples into different categories according to the shade guide used. The statistical classification algorithm is preferably Support Vector Machines (SVM) according to the invention. Other statistical classification algorithms, including but not limited to neural network (multi-layer perception), k-nearest neighbors, Gaussian mixture model, Gaussian, naive Bayes, decision tree, and radial basis function classifiers, are possible for the invention.

The three to five shade tabs having the descriptors which are the most similar to the target tooth are selected at step 65 for further visual reference at the dental chair side or for fabrication of dental ceramic in laboratory.

If enhanced communication between the dentist and the technician in the laboratory is necessary, the above steps may be repeated by placing the selected three or five shade tabs on the tab holder 9 and taking new precise images once again to select the optimal shade tab among the used shade tabs.

Technical Effects of the Invention

The dental shade matching device of the invention helps communication between the dentists and the dental technicians over the restorative prosthesis fabrication. The dentists can easily capture the images of the target tooth with its surrounding structure even without the need of grasping the knowledge of color science. The device of the invention will automatically select the optimal shade color and translucency using the programmed dental color measurement algorithm. If required by the dentists, the shade tabs can be placed inside the image for real-time comparison. Moreover, during the communication, the technicians can capture the images using the same device in the laboratory before the finished prostheses being sent back to the clinic. The advantages of the device include one or more of the following:

1. The non-contact type CCD/CMOS image sensor is used to provide an easy-to-use (the same way as using consumer digital camera) and low-cost solution to the dental professionals. Moreover, the captured image possesses various data, including the information on the region of the tooth going to be matched, surface texture, surrounding teeth and soft tissue morphology that are important for achieving the optimal prosthesis. The shade tab can be also included in the same image for reference and confirmation.

2. The external illuminant variation from capturing sites is eliminated, no matter it originates from the different clinics or laboratories. The captured region is segregated by the opaque cover shield body, so that the external illuminant variation onto the tooth surface is avoided.

3. Multiple chromatic illuminant shedding is provided. In the device of the invention, different chromatic illuminants provided by the illuminant module enhance the result of color matching under more than one visible light frequency. This design helps to select the tooth color that should be similar under different lighting conditions, such as sunny day, cloudy day, night time, warm light, fluorescent light and the like. More specifically, it solves the problem of the different light reflection properties between the tooth and the dental materials, which is caused by metamerism effect, and ensures the fabricated porcelain/restorative material having the similar reflective properties under different lighting conditions.

4. Specially designed translucency feature is provided. The translucent illuminant module enables to acquire the translucency information of the target tooth and the prosthesis.

5. The operation of the device is easy and simple. The device is a Plug-and-Play design and can be operated through touch screen or control panel, thereby reducing the chair-side operation time.

6. The images and data are digital and can be electronically transferable to an external system, for example to the computers, servers or any web locations through for example Wi-Fi, Bluetooth, GPRS protocols.

7. The device of the invention allows the readout of the color and translucency information of the target tooth and the shade tab, or the readout of the color and translucency information of the target tooth in the absence of the shade tab. The device of the invention also allows the readout and comparison of the color and translucency information of the target tooth and the fabricated prostheses, so that any possible error in the fabricated prostheses may be corrected in situ after it is fabricated.

Thus, the invention improves the quality of dental prosthetic therapy and helps the dentists to make a suitable and easy decision on dental color for the prosthesis fabrication. With the device of the invention, the dental shade communications between the clinical professionals and the technicians are greatly enhanced. It makes the application of non-contact type CCD/CMOS sensors in the dental color matching possible.

The currently available dental spectrophotometers are expensive, but the device of the invention costs substantially lower than the price of these current instruments. With the newly developed dental color matching algorithm, the invention allows to achieve much better matching accuracy, since the algorithm can have good control of most variation factors.

Moreover, the new concept of shade matching through multiple chromatic illuminants devised in the invention enables the final prostheses having a narrow range of metamerism effect. The translucent illuminant module behind the target tooth and the shade tabs results in the finished crown restoration which not only has a perfect color match, but also has their translucency properties that cannot be acquired by any other color matching devices in the art. Due to the unique features provided by the invention, local technicians can take oversea denture orders and provide perfect dental color matching without meeting the patients in person. Since esthetic dentistry is the most popular topic nowadays and it has great dental treatment market shares. The invention helps the dentist to deliver high quality prostheses that meet the patients' esthetic requirements.

The device of the invention utilizes the low-cost non-contact type CCD/CMOS-based camera for the dental shade matching. The device, when used in combination with the new matching calculations described above, may have better accuracy and technology than the commercialized products in the art. The advantages of the inventive device over the prior art commercial products are given in Table 1 below.

TABLE 1

| | Difference | Commercial Products | Inventive Device |
|---|---|---|---|
| 1 | Sensor type | Contact-type Spectrophotometer/colorimeter | Non-contact type CCD/CMOS-based |
| 2 | Calculating feature | Either in La*b* or HSV color space | Computing any combination of color features from different color spaces La*b*, HSV, RGB, XYZ |
| 3 | Measuring window size | Restriction to small window view of spectrophotometer/colorimeter, failure to measure the entire tooth surface | No restriction on measuring size of tooth surface |
| 4 | Content of measurement | Only specified color features can be measured | All color features, surface, texture, color gradation and neighboring teeth for reference |
| 5 | Solution to metamerism effect | Nil | Acquire the color information of the materials through a series of images captured in different chromatic illuminants |
| 6 | Translucency measurement | Indirect measurement of image grayscale intensity | Direct measurement of the translucency through a translucent illuminant behind the tooth and/crown fabrication |
| 7 | Real time shade reference | Nil | Real shade tabs can be shown in the image |
| 8 | Measuring algorithm | Measuring ΔE or mean value of color features to insufficiently represent an area of color | Automatic color content retrieval and model-based matching algorithm, detail description of tooth surface by its color features, surface texture and color gradation |

While the embodiments described herein are intended as an exemplary dental shade matching device, it will be appreciated by those skilled in the art that the present invention is not limited to the embodiments illustrated. Those skilled in the art will envision many other possible variations and modifications by means of the skilled person's common knowledge without departing from the scope of the invention, however, such variations and modifications should fall into the scope of this invention.

What is claimed is:

1. A dental shade matching device, comprising: a camera body to capture an image of one or more target teeth, and having at least one chromatic illuminant module to emit chromatic light that provides specific frequencies of visible light emitted at sequential time intervals, and the camera body captures a series of images under all these illumination separately or sequentially; an opaque intra-oral compartment snugly adapted to be received in a human mouth, said intra-oral compartment having a soft tissue retracting part for retracting the soft tissue around the target tooth, and a stop for supporting the target teeth in a desirable orientation; an opaque cover shield body having one end attached tightly to the camera body and another end connected to the intra-oral compartment; one or more holders for holding one or more shade tabs in place and releasably attached to the intra-oral compartment; and a color matching module comprising a microprocessor, said color matching module being operably connected to the camera body to receive the captured images containing color and translucency information of the target tooth and/or shade tabs, and then to process the images based on a content-based algorithm for automatic shade matching between the target tooth and the shade tabs for each of the captured images, so as to achieve an optimal dental prosthesis.

2. The dental shade matching device according to claim 1, wherein the soft tissue retracting part is used as a lip retractor for placement on the target tooth in the mouth.

3. The dental shade matching device according to claim 1, further comprising a translucent illuminant module placed on the stop of the intra-oral compartment.

4. The dental shade matching device according to claim 3, wherein the stop is an incisal/occlusal stop having a protrusion extending toward the mouth, and the translucent illuminant module is placed on the protrusion.

5. The dental shade matching device according to claim 1, wherein the color and translucency information of the target tooth and/or the shade tabs are processed in situ or electronically transferred to an external system where the images are processed.

6. The dental shade matching device according to claim 1, wherein the chromatic illuminant modules are installed in a ring-shape mount to surround a lens of the camera body.

7. The dental shade matching device according to claim 1, wherein the holder is formed as a supporting space for holding a rod or strip of the shade tab.

8. The dental shade matching device according to claim 1, wherein the content-based algorithm comprises: image pre-processing where each of the images is segmented into a plurality of sections and noise is removed, color features extraction where color features of the image are extracted and reassembled into a plurality of color feature sets, and similarity measurement where the target tooth and the shade tabs are compared and analyzed for their contents to determine an optimal shade candidate.

9. The dental shade matching device according to claim 8, wherein for each of the images, only a part of the target tooth or the shade tab, which is not influenced by light shadow on the lateral and cervical borders of the tab or the target tooth, is cropped to represent its content.

10. The dental shade matching device according to claim 9, wherein the noise arising from over-reflection of flashlight on contour areas is removed, so that refined color contents are used for further shade matching.

11. The dental shade matching device according to claim 8, wherein the contents of the target tooth are divided into an array of blocks, each of which is analyzed for comparison of the color features with the shade tabs.

12. The dental shade matching device according to claim 11, wherein one or more virtual color spaces are used in the algorithm for tooth color measurement, the color features in the color spaces are extracted from each of the blocks, and the statistic measurements for the similarity measurement are calculated for the block to describe the color feature thereof.

13. The dental shade matching device according to claim 12, wherein the virtual color space is constructed by one or more vector of different color space systems selected from the group consisting of color spaces: HSV, RGB, XYZ, Lab and Luv, or a combination thereof.

14. The dental shade matching device according to claim 12, wherein the virtual color space is selected from: Sa*b* color space, wherein S comes from HSV space, a* and b* come from L*a*b* space, and wherein S means saturation representing the degree of color saturation, a* represents a measurement of the redness (+a*) to the greenness (−a*), and b* represents a measurement of the yellowness (+b*) to the blueness (−b*).

15. The dental shade matching device according to claim 12, wherein the color matching module performs the calculations for each of the above virtual color spaces using a statistic training/prediction method, preferably Support Vector Machine (SVM), to compare results of the color matching obtained from the virtual color spaces, thereby selecting the optimal color space for fabrication of the dental prosthesis.

16. The dental shade matching device according to claim 12, wherein a difference of the content is defined as a summation of all individual block distances within the content, and the similarity between two contents is measured by measurements of the block distances, and the distances between the two corresponding blocks in contents s and t is defined as: dist(s,t)=(.SIGMA..sub.i(b.sup.s(i)−b.sup.t(i)).sup.2).sup.½, where i is the block label within the content, 1.ltoreq.i.l-toreq.m.times.n; b.sup.s and b.sup.t are the blocks in contents s and t, respectively.

17. The dental shade matching device according to claim 8, wherein a statistical classification algorithm selected from the group consisting of: Support Vector Machines (SVM), neural network (multi-layer perception), k-nearest neighbors, Gaussian mixture model, Gaussian, naive Bayes, decision tree, radial basis function classifiers, and any combination thereof, is used in the algorithm.

18. The dental shade matching device according to claim 8, wherein the color matching module is programmed to produce various prosthesis models according to existing data stored therein, and the captured color and translucency information is compared and analyzed directly with the produced models for the automatic shade matching between the target tooth and the shade tabs.

19. The dental shade matching device according to claim 1, wherein the camera body is a CCD/CMOS-based digital camera.

20. The dental shade matching device according to claim 1, wherein the content-based algorithm is a content-based image retrieval (CBIR) algorithm.

21. A dental shade matching device, comprising: a camera body to capture an image of one or more target teeth, and having at least one chromatic illuminant module to emit chromatic light; an opaque intra-oral compartment snugly adapted to be received in a human mouth, said intra-oral compartment having a soft tissue retracting part for retracting the soft tissue around the target tooth, and a stop for supporting the target teeth in a desirable orientation; an opaque cover shield body having one end attached tightly to the camera body and another end connected to the intra-oral compartment; one or more holders for holding one or more shade tabs in place and releasable attached to the intra-oral compartment; and a color matching module comprising a microprocessor, said color matching module being operably connected to the camera body to receive the captured images containing color and translucency information of the target tooth and/or shade tabs, and then to process the images based on a content-based algorithm for automatic shade matching between the target tooth and the shade tabs for each of the captured images, so as to achieve an optimal dental prosthesis wherein the content-based algorithm includes: image preprocessing where each of the images is segmented into a plurality of sections and noise is removed, color features extraction where color features of the image are extracted and reassembled into a plurality of color feature sets, and similarity measurement where the target tooth and the shade tabs are compared and analyzed for their contents to determine an optimal shade candidate.

* * * * *